US010091983B2

(12) United States Patent
Allen-Hoffmann et al.

(10) Patent No.: US 10,091,983 B2
(45) Date of Patent: Oct. 9, 2018

(54) CRYOPRESERVATION OF VIABLE HUMAN SKIN SUBSTITUTES

(71) Applicant: STRATATECH CORPORATION, Madison, WI (US)

(72) Inventors: B. Lynn Allen-Hoffmann, Madison, WI (US); John C. Pirnstill, Fitchburg, WI (US); Kenneth R. Gratz, Madison, WI (US); Allen R. Comer, Madison, WI (US)

(73) Assignee: Stratatech Corporation, Madison, WI (US)

( * ) Notice: Subject to any disclaimer, the term of this patent is extended or adjusted under 35 U.S.C. 154(b) by 0 days.

(21) Appl. No.: 14/208,439

(22) Filed: Mar. 13, 2014

(65) Prior Publication Data

US 2014/0271583 A1    Sep. 18, 2014

Related U.S. Application Data

(60) Provisional application No. 61/779,661, filed on Mar. 13, 2013.

(51) Int. Cl.
*A01N 1/02* (2006.01)

(52) U.S. Cl.
CPC ................................. *A01N 1/0221* (2013.01)

(58) Field of Classification Search
None
See application file for complete search history.

(56) References Cited

U.S. PATENT DOCUMENTS

| | | | |
|---|---|---|---|
| 5,145,770 A * | 9/1992 | Tubo | A01N 1/0221 424/574 |
| 5,518,878 A * | 5/1996 | Wilkins | A01N 1/0221 435/1.3 |
| 5,689,961 A * | 11/1997 | Cosman | A01N 1/02 62/373 |
| 5,891,617 A | 4/1999 | Watson et al. | |
| 6,110,208 A | 8/2000 | Soranzo et al. | |
| 6,846,675 B2 | 1/2005 | Conrad et al. | |
| 6,974,697 B2 | 12/2005 | Comer et al. | |
| 7,407,805 B2 | 8/2008 | Comer et al. | |
| 7,462,448 B2 | 12/2008 | Allen-Hoffmann et al. | |
| 7,498,167 B2 | 3/2009 | Comer et al. | |
| 7,501,238 B2 | 3/2009 | Comer et al. | |
| 7,541,188 B2 | 6/2009 | Conrad et al. | |
| 7,674,291 B2 | 3/2010 | Centanni et al. | |
| 7,807,148 B2 | 10/2010 | Comer et al. | |
| 7,888,496 B2 | 2/2011 | Allen-Hoffmann et al. | |
| 7,915,042 B2 | 3/2011 | Comer et al. | |
| 7,955,790 B2 | 6/2011 | Comer et al. | |
| 7,988,959 B2 | 8/2011 | Comer et al. | |
| 8,092,531 B2 | 1/2012 | Centanni et al. | |
| 8,580,314 B2 | 11/2013 | Comer et al. | |
| 8,685,463 B2 | 4/2014 | Comer et al. | |
| 8,790,636 B2 | 7/2014 | Centanni et al. | |
| 8,808,685 B2 | 8/2014 | Comer et al. | |
| 8,992,997 B2 | 3/2015 | Comer et al. | |
| 2002/0192197 A1 * | 12/2002 | Kuri-Harcuch | A61L 27/60 424/93.21 |
| 2004/0053409 A1 | 3/2004 | Tai et al. | |
| 2005/0144657 A1 * | 6/2005 | Ozbun | A01K 67/027 800/9 |
| 2006/0222635 A1 | 10/2006 | Centanni et al. | |
| 2006/0257383 A1 | 11/2006 | Allen-Hoffmann et al. | |
| 2006/0258001 A1 | 11/2006 | Allen-Hoffmann et al. | |
| 2009/0145087 A1 | 6/2009 | Allen-Hoffmann et al. | |
| 2010/0119615 A1 | 5/2010 | Comer et al. | |
| 2010/0330046 A1 | 12/2010 | Comer et al. | |
| 2013/0108670 A1 | 5/2013 | Lynch et al. | |
| 2013/0108683 A1 | 5/2013 | Lynch | |
| 2014/0335064 A1 | 11/2014 | Centanni et al. | |
| 2015/0196686 A1 | 7/2015 | Comer et al. | |

FOREIGN PATENT DOCUMENTS

| | | |
|---|---|---|
| WO | 95/07611 | 3/1995 |
| WO | 96/14738 | 5/1996 |
| WO | 96/24018 | 8/1996 |
| WO | 96/33750 | 10/1996 |
| WO | 97/28402 | 8/1997 |
| WO | 02/058588 | 8/2002 |
| WO | 2008/088136 | 7/2008 |
| WO | 2009/065005 | 5/2009 |

OTHER PUBLICATIONS

International Search Report and Written Opinion, PCT/US14/25599, dated Aug. 25, 2014.
Bondoc, CC, et al., "Clinical Experience With Viable Frozen Human Skin and a Frozen Skin Bank," 1971, Ann. Surg. vol. 174, No. 3; pp. 371-381, p. 373, left column paragraph 1; p. 373, figure 3.
Extended European Search Report dated Oct. 26, 2016 from related EP Patent Application No. 14775892.4; 29 pgs.
Hans-Jurgen Stark et al. "Organotypic cocultures as skin equivalents: A complex and sophisticated in vitro system", Biological Procedures Online, vol. 19, No. 4, Apr. 12, 2004, pp. 55-60.
Rupf et al. "Cryopreservation of Organotypical Cultures Based on 3D Scaffolds" Cryoletters, Mar. 1, 2010, pp. 157-168.
Demetrulias et al. "Skin2®—an in vitro human skin model: the correlation between in vivo and in vitro testing of surfactants" Exp. Dermatol., Jan. 1,1998, pp. 18-26.
Examination Report dated Sep. 7, 2017 from related EP Patent Application No. 14775892.4; 11 pgs.
Examination Report dated Oct. 25, 2017 from related CA Patent Application No. 2905656; 3 pgs.
Examination Report dated Feb. 20, 2018 from related JP Patent Application No. 2016-501891; 11 pgs.

* cited by examiner

*Primary Examiner* — Christopher M Babic
*Assistant Examiner* — Kimberly A Aron

(57) ABSTRACT

The present invention relates generally to systems and methods for preparing, storing, shipping and using skin equivalents made by organotypic culture. In particular, the present invention relates to systems and methods for cryopreserving viable skin substitutes.

9 Claims, 10 Drawing Sheets

CRYOPRESERVATION OF VIABLE HUMAN SKIN SUBSTITUTES

CROSS-REFERENCE TO RELATED APPLICATIONS

This application claims priority to pending U.S. Provisional Patent Application No. 61/779,661 filed Mar. 13, 2013, the content of which is incorporated by reference herein in its entirety.

FIELD OF THE INVENTION

The present invention relates generally to systems and methods for cryopreservation of viable human skin substitutes.

BACKGROUND

The emerging field of tissue engineering (TE) is poised to make enormous progress in the treatment of organ disease and dysfunction in the coming decade. In 2001, there were 23 cell-based therapeutics approved for market in the United States (U.S.) and Europe, of which nine were skin substitutes or grafts, and 100 more products were in development. (De Bree, Genomics-based Drug Data Report and Regenerative Therapy (1) 2:77-96 (2001)). A decade later, engineered tissues have emerged as a discrete industry sector within the wound care industry and represent one of regenerative medicine's most promising cell based therapeutic platforms. The global wound care market was estimated to be $16.8 billion in 2012 and has been growing at a rate of approximately 6% annually (Kalorama Information, April 2012). The bulk of this market is comprised of traditional sectors that are mature and highly competitive, and include products targeting basic and advanced wound care, wound closure, and anti-infectives. This has led competitors to increasingly focus their attention on developing highly differentiated products in the more innovative active wound care sector, a sector that represents approximately 15% of the overall market. While sales of negative pressure wound therapy still predominate, 2010 sales of engineered tissues and other products within the U.S. biologics market grew to $448 million, and are projected to increase to $1.058 billion by 2015, a compound annual growth rate of 18.8% (BioMedGPS-SmarTRAK market analysis, 2012).

Although a multitude of revolutionary and economically important applications for engineered tissues and organs exist in the human health arena, the full economic potential of the industry is far from realized. At present, only two tissue engineering companies worldwide have been able to commercialize cell based, skin substitute products focused on cutaneous wound healing and achieve annual sales in excess of $100 million.

A major impediment to the acceptance of engineered tissues by medical practitioners, healthcare providers, and second party payers is the lack of a means to effectively and efficiently preserve and store engineered tissues. The nature of living cells and tissue products makes development of long-term storage challenging. Current engineered tissues must often be stored and shipped under carefully controlled conditions to maintain viability and function. Typically, engineered tissue products take weeks or months to produce but must be used within hours or days after manufacture. As a result, TE companies must continually operate with their production facilities at top capacity and absorb the costs of unsold product which must be discarded. These inventory losses, on top of already costly manufacturing process, have forced prices to impractical levels. As one specific example, APLIGRAF requires about four weeks to manufacture, is usable for only 15 days and must be maintained between 20 and 23° C. until used. As another example, EPICEL is transported by a nurse from Genzyme Biosurgery's production facility in Cambridge, Mass. to the point of use in a portable incubator and is used immediately upon arrival. Such constraints represent significant challenges to developing convenient and cost-effective products.

Cryopreservation has been explored as a solution to the storage problem, but it is known to induce tissue damage through ice formation, chilling injury, and osmotic imbalance. Besides APLIGRAF, the only other approved living skin equivalent, ORCEL, has been evaluated as a frozen product but had the drawback that it must be maintained at temperatures below −100° C. prior to use. This requires specialized product delivery and storage conditions, including the use of dangerous goods during transport, and use of liquid nitrogen for storage, which is expensive, dangerous, and not readily available in rural clinics and field hospitals.

Accordingly, what is needed in the art are improved methods of cryopreserving viable engineered tissues and cells for storage under conditions that are routinely available at the point of use.

SUMMARY OF THE INVENTION

The present invention relates generally to systems and methods for cryopreservation of viable human skin substitutes.

In some embodiments, the present invention provides methods of cryopreserving an organotypically cultured skin equivalent to maintain viable tissue comprising: treating an organotypically cultured skin equivalent in a cryoprotectant solution in a single step; packaging the organotypically cultured skin equivalent to provide a packaged skin equivalent; and freezing the organotypically cultured skin equivalent to provide a packaged cryopreserved skin equivalent. In some embodiments, the cryoprotectant is provided in a solution comprising about 20% or 21% to about 70% of the solution by volume, and more preferably about 20% or 21% to about 45% of the solution by volume or 37.5% to 62.5% of the solution by volume, or most preferably from about 25% to 40% of the solution by volume or 42.5% to 57.5% of the solution by volume, depending on the temperature. In some embodiments, the treatment with cryoprotectant is conducted at from about 2 C to 8 C, while in other embodiments, the treatment step is conducted at room temperature, for example from about 15 C to 30 C. In some embodiments, the cryoprotectant is glycerol. In some embodiments, the freezing further comprises freezing the organotypically cultured skin equivalent in the absence of substantial excess cryoprotectant. In some embodiments, the freezing further comprises freezing at about −80 C. In some embodiments, the freezing further comprises direct exposure to temperatures ranging from about −50 C to −100 C. In some embodiments, the packaging further comprises enclosing the cryopreserved skin equivalent in a sterile bag and enclosing the sterile bag in a second bag. In some embodiments, the organotypically cultured skin equivalents comprise NIKS cells. In some embodiments, the NIKS cells comprise an exogenous nucleic acid sequence encoding an exogenous polypeptide. In some embodiments, the skin equivalent retains viability after thawing. In some embodiments, the skin equivalent has an $A_{550}$ of at least 50% of a reference skin equivalent as determined by an MTT assay.

In some embodiments, the methods further comprising thawing said cryopreserved skin equivalent and applying said thawed skin equivalent to a patient in need thereof, wherein said thawed skin equivalent is not rinsed prior to said application to said patient. In some embodiments, the present invention provides methods of thawing a cryopreserved skin equivalent prior to application to a subject, comprising: warming the cryopreserved skin equivalent; and contacting the cryopreserved skin equivalent with a diffusion mediator comprising a tissue compatible solution to allow removal of the cryoprotectant solution by diffusion. In some embodiments, the warming comprises exposure to room temperature at the site of use. In some embodiments, the diffusion mediator is selected from the group consisting of an absorbent medium, a membrane, and a dialysis bag. In some embodiments, the absorbent medium is selected from the group consisting of Telfa pads, foam pads, gauze pads, and cellulosic pads containing the tissue compatible medium. In some embodiments, the tissue compatible solution is a buffered solution.

In some embodiments, the present invention provides methods of treating a subject comprising providing a packaged cryopreserved skin equivalent produced as described above; aseptically transferring the cryopreserved skin equivalent from the package; warming the cryopreserved skin equivalent; contacting the cryopreserved skin equivalent with an absorbent medium comprising a tissue compatible solution to allow removal of the cryoprotectant solution by diffusion; and applying the cryopreserved skin equivalent to the subject.

In some embodiments, the present invention provides a cryopreserved skin equivalent equilibrated with a cryoprotectant, the skin equivalent being substantially free of excess cryoprotectant on the exterior surface of the skin equivalent. In some embodiments, the present invention provides a system comprising the foregoing skin equivalent disposed on an absorbent medium.

In some embodiments, the present invention provides methods comprising providing the packaged cryopreserved skin equivalent as described above; and applying the skin equivalent to a wound under conditions such that the skin equivalent contacts the wound.

In some embodiments, the present invention provides a kit comprising a cryopreserved skin substitute, an absorbent medium, and a tissue compatible solution. In some embodiments, the cryopreserved skin substitute is packaged in a sealable enclosure. In some embodiments, the cryopreserved skin substitute is provided in a culture vessel packaged in the bag.

In some embodiments, the present invention provides a method comprising: providing a culture dish comprising a cell culture substrate movable between defined upper and lower positions in the culture dish, forming a skin equivalent on the cell culture substrate, wherein the cell culture substrate is at the upper position, lowering the cell culture substrate to the lower position for further processing. In some embodiments, the further processing comprises treating the skin equivalent with a cryoprotectant solution. In some embodiments, the further processing comprises freezing the skin equivalent in the culture dish.

In some embodiments, the present invention provides a method of producing a cryopreserved skin equivalent comprising: providing a culture dish comprising an insert movable between upper and lower positions in the culture dish, the insert having a bottom planar surface formed from a porous membrane, forming a dermal equivalent comprising fibroblast cells on the porous membrane in the insert, wherein the insert is placed the upper position the culture dish, culturing the fibroblast cells to form a dermal equivalent, applying keratinocyte cells to the dermal equivalent, culturing the keratinocytes in a culture medium under conditions such that the keratinocytes form a skin equivalent comprising stratified epithelium, removing the culture medium, lowering the insert to the lower position, treating the skin equivalent with a cryoprotectant solution, and freezing the skin equivalent in the culture dish.

In some embodiments, the present invention provides methods of treating a patient in need thereof with a cryopreserved skin equivalent made by the foregoing methods comprising thawing said cryopreserved skin equivalent and applying said thawed skin equivalent to said patient in need thereof, wherein said thawed skin equivalent is not rinsed prior to said application to said patient.

DEFINITIONS

Figure 1:
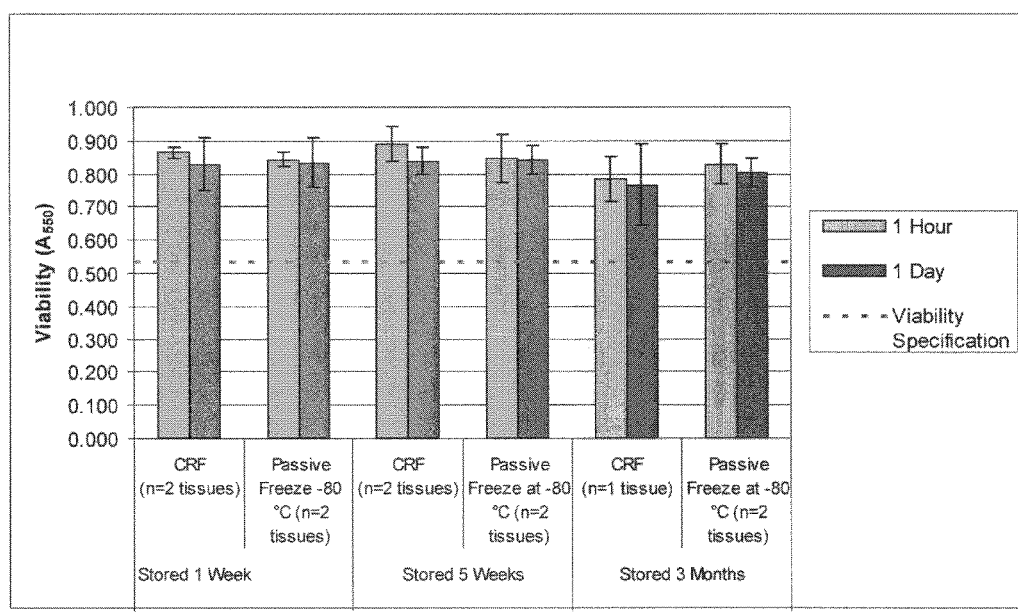
FIG. 1 is a graph of viability testing of thawed tissues using the MTT assay. The tissues were cryopreserved using a controlled-rate freezer (CRF) or by passive freezing in an ultra-cold freezer (set to −80° C.) and stored for up to 3 months, then thawed and analyzed at 1 hour and 1 day. Viability was measured by MTT analysis of three 0.5 cm$^2$ punches from each 44 cm$^2$ tissue at each time point (mean+/−1 st. dev.).

As used herein, the terms "skin equivalent", "human skin equivalent", "human skin substitute", and "organotypic cultures" are used interchangeably to refer to an in vitro derived culture of keratinocytes that has stratified into squamous epithelia. Typically, the skin equivalents are produced by organotypic culture and include a dermal layer in addition to a keratinocyte layer.

As used herein, the term "sterile" refers to a skin equivalent that is essentially or completely free of detectable microbial or fungal contamination.

As used herein, the term "NIKS cells" refers to cells having the characteristics of the cells deposited as cell line ATCC CRL-1219. NIKS stands for near-diploid immortalized keratinocytes.

As used herein, the term "viable" when used in reference to a skin equivalent refers to the viability of cells in the skin equivalent following cryopreservation. In preferred embodiments, a "viable" skin has an $A_{550}$ of at least 50%, 60%, 70%, 80% or 90% of a control non-cryopreserved tissue as measured by an MTT assay or at least 50%, 60%, 70%, 80% or 90% of the readout value of a similar viability assay.

DETAILED DESCRIPTION

The present invention relates generally to systems and methods for cryopreservation of human skin substitutes. In particular, the present invention relates to methods for cryopreserving viable human skin equivalents so that they can be stored for prolonged periods at the site of use, such as a hospital, operating room or burn unit. The methods disclosed herein allow for novel increases in efficiency of the preservation process and utilization of preserved skin equivalents, including single-step equilibration in a cryoprotectant, packaging of the skin equivalent in a sterile package prior to cryropreservation, and the ability to use the cryopreserved tissues for direct application to a patient (e.g., in a grafting procedure) without rinsing. In some embodiments, the present invention provides ready-to-use cryopreserved skin equivalents for use in treatment of a patient, and in preferred embodiments for use in grafting procedures. The cryopreserved skin equivalent is designed for long term storage at the site of use. In some embodiments, the cryopreserved equivalents are engineered to deliver the broad spectrum human host defense peptides such as β-defensin-3 (hBD-3) or cathelicidin (hCAP18/LL-37), or pro-angiogenic factors, to the wound bed.

Previously, cadaver skin has been harvested and cryopreserved by treatment with from 10% to 20% glycerol as a cryopreservative. See e.g., Kagan et al., Clin Lab Med 25 (2005) 587-605. Surprisingly, it has been found that increased glycerol concentrations are needed to cryopreserve human skin equivalents.

Accordingly, in some embodiments, the present invention provides a cryopreserved skin equivalent. In some embodiments, the skin equivalent has been engineered to express and provide exogenous antimicrobial polypeptides or pro-angiogenic factors. The present invention is not limited to the use of any particular antimicrobial polypeptide. In preferred embodiments, the antimicrobial polypeptide is human β-defensin-1, human β-defensin-2, human β-defensin-3, or cathelicidin (hCAP-18/LL37) or variant. In some preferred embodiments, nucleic acid constructs or vectors encoding the antimicrobial polypeptide or pro-angiogenic factor are introduced into the keratinocytes (e.g., NIKS cells) and the transfected keratinocytes are used to make the skin equivalent by organotypic culture techniques. Preferred embodiments for the production of skin equivalents expressing exogenous polypeptides, as well as additional wild-type and variant antimicrobial polypeptides can be found in U.S. Pat.

Nos. 7,674,291; 7,807,148; 7,915,042; 7,988,959; and 8,092,531; each of which is incorporated herein by reference in its entirety.

In some embodiments, the cryopreserved skin equivalents are applied to wounds after thawing and left in place. In other embodiments, the cryopreserved skin equivalents are applied temporarily to wounds. In some embodiments, the cryopreserved skin equivalents are removed and replaced with additional cryopreserved human skin equivalents.

A) Skin Equivalents Produced by Organotypic Culture

The present invention is not limited to the use of any particular source of cells that are capable of differentiating into squamous epithelia. Indeed, the present invention contemplates the use of a variety of cell lines and sources that can differentiate into squamous epithelia, including both primary and immortalized keratinocytes. Sources of cells include keratinocytes and dermal fibroblasts biopsied from humans and cavaderic donors (Auger et al., In Vitro Cell. Dev. Biol.—Animal 36:96-103; U.S. Pat. Nos. 5,968,546 and 5,693,332, each of which is incorporated herein by reference), neonatal foreskins (Asbill et al., Pharm. Research 17(9): 1092-97 (2000); Meana et al., Burns 24:621-30 (1998); U.S. Pat. Nos. 4,485,096; 6,039,760; and 5,536,656, each of which is incorporated herein by reference), and immortalized keratinocytes cell lines such as NM1 cells (Baden, In Vitro Cell. Dev. Biol. 23(3):205-213 (1987)), HaCaT cells (Boucamp et al., J. cell. Boil. 106:761-771 (1988)); and NIKS cells (Cell line BC-1-Ep/SL; U.S. Pat. No. 5,989,837, incorporated herein by reference; ATCC CRL-12191). Each of the mentioned cell lines can be cultured or genetically modified in order to produce a cell line capable of expressing or co-expressing the desired protein(s). In particularly preferred embodiments, NIKS cells are utilized. The discovery of the novel NIKS human keratinocyte cell line provides an opportunity to genetically engineer human keratinocytes with non-viral vectors. A unique advantage of the NIKS cells is that they are a consistent source of genetically-uniform, pathogen-free human keratinocytes. For this reason, they are useful for the application of genetic engineering and genomic gene expression approaches to provide human skin equivalents with enhanced properties over currently available skin equivalents. NIKS cells, identified and characterized at the University of Wisconsin, are nontumorigenic, karyotypically stable, and exhibit normal growth and differentiation both in monolayer and organotypic culture. NIKS cells form fully stratified skin equivalents in culture. These cultures are indistinguishable by all criteria tested thus far from organotypic cultures formed from primary human keratinocytes. Unlike primary cells however, NIKS cells exhibit an extended lifespan in monolayer culture. This provides an opportunity to genetically manipulate the cells and isolate new clones of cells with new useful properties (Allen-Hoffmann et al., J. Invest. Dermatol., 114(3): 444-455 (2000)).

The NIKS cells arose from the BC-1-Ep strain of human neonatal foreskin keratinocytes isolated from an apparently normal male infant. In early passages, the BC-1-Ep cells exhibited no morphological or growth characteristics that were atypical for cultured normal human keratinocytes. Cultivated BC-1-Ep cells exhibited stratification as well as features of programmed cell death. To determine replicative lifespan, the BC-1-Ep cells were serially cultivated to senescence in standard keratinocyte growth medium at a density of $3\times10^5$ cells per 100-mm dish and passaged at weekly intervals (approximately a 1:25 split). By passage 15, most keratinocytes in the population appeared senescent as judged by the presence of numerous abortive colonies which exhibited large, flat cells. However, at passage 16, keratinocytes exhibiting a small cell size were evident. By passage 17, only the small-sized keratinocytes were present in the culture and no large, senescent keratinocytes were evident. The resulting population of small keratinocytes that survived this putative crisis period appeared morphologically uniform and produced colonies of keratinocytes exhibiting typical keratinocyte characteristics including cell-cell adhesion and apparent squame production. The keratinocytes that survived senescence were serially cultivated at a density of $3\times10^5$ cells per 100-mm dish. Typically the cultures reached a cell density of approximately $8\times10^6$ cells within 7 days. This stable rate of cell growth was maintained through at least 59 passages, demonstrating that the cells had achieved immortality. The keratinocytes that emerged from the original senescencing population are now termed NIKS. The NIKS cell line has been screened for the presence of proviral DNA sequences for HIV-1, HIV-2, EBV, CMV, HTLV-1, HTLV-2, HBV, HCV, B-19 parvovirus, HPV-16, SV40, HHV-6, HHV-7, HPV-18 and HPV-31 using either PCR or Southern analysis. None of these viruses were detected.

Chromosomal analysis was performed on the parental BC-1-Ep cells at passage 3 and NIKS cells at passages 31 and 54. The parental BC-1-Ep cells have a normal chromosomal complement of 46, XY. At passage 31, all NIKS cells contained 47 chromosomes with an extra isochromosome of the long arm of chromosome 8. No other gross chromosomal abnormalities or marker chromosomes were detected. The karyotype of the NIKS cells has been shown to be stable to at least passage 54.

The DNA fingerprints for the NIKS cell line and the BC-1-Ep keratinocytes are identical at all twelve loci analyzed demonstrating that the NIKS cells arose from the parental BC-1-Ep population. The odds of the NIKS cell line having the parental BC-1-Ep DNA fingerprint by random chance is $4\times10^{-16}$. The DNA fingerprints from three different sources of human keratinocytes, ED-1-Ep, SCC4 and SCC13y are different from the BC-1-Ep pattern. This data also shows that keratinocytes isolated from other humans, ED-1-Ep, SCC4, and SCC13y, are unrelated to the BC-1-Ep cells or each other. The NIKS DNA fingerprint data provides an unequivocal way to identify the NIKS cell line.

Loss of p53 function is associated with an enhanced proliferative potential and increased frequency of immortality in cultured cells. The sequence of p53 in the NIKS cells is identical to published p53 sequences (GenBank accession number: M14695). In humans, p53 exists in two predominant polymorphic forms distinguished by the amino acid at codon 72. Both alleles of p53 in the NIKS cells are wild-type and have the sequence CGC at codon 72, which codes for an arginine. The other common form of p53 has a proline at this position. The entire sequence of p53 in the NIKS cells is identical to the BC-1-Ep progenitor cells. Rb was also found to be wild-type in NIKS cells.

Anchorage-independent growth is highly correlated to tumorigenicity in vivo. For this reason, the anchorage-independent growth characteristics of NIKS cells in agar or methylcellulose-containing medium were investigated. NIKS cells remained as single cells after 4 weeks in either agar- or methylcellulose-containing medium. The assays were continued for a total of 8 weeks to detect slow growing variants of the NIKS cells. None were observed.

To determine the tumorigenicity of the parental BC-1-Ep keratinocytes and the immortal NIKS keratinocyte cell line, cells were injected into the flanks of athymic nude mice. The human squamous cell carcinoma cell line, SCC4, was used as a positive control for tumor production in these animals. The injection of samples was designed such that animals received SCC4 cells in one flank and either the parental BC-1-Ep keratinocytes or the NIKS cells in the opposite flank. This injection strategy eliminated animal to animal variation in tumor production and confirmed that the mice would support vigorous growth of tumorigenic cells. Neither the parental BC-1-Ep keratinocytes (passage 6) nor the NIKS keratinocytes (passage 35) produced tumors in athymic nude mice.

NIKS cells were analyzed for the ability to undergo differentiation in both submerged culture and organotypic culture. Techniques for organotypic culture are described in detail in the examples. In particularly preferred embodiments, the organotypically cultured skin equivalents of the present invention comprise a dermal equivalent formed from collagen or a similar material and fibroblasts. The keratinocytes, for example NIKS cells or a combination of NIKS cells and cells from a patient are seeded onto the dermal equivalent and form an epidermal layer characterized by squamous differentiation following the organotypic culture process.

For cells in submerged culture, the formation cornified envelopes was monitored as a marker of squamous differentiation. In cultured human keratinocytes, early stages of cornified envelope assembly result in the formation of an immature structure composed of involucrin, cystatin-α and other proteins, which represent the innermost third of the mature cornified envelope. Less than 2% of the keratinocytes from the adherent BC-1-Ep cells or the NIKS cell line produce cornified envelopes. This finding is consistent with previous studies demonstrating that actively growing, subconfluent keratinocytes produce less than 5% cornified envelopes. To determine whether the NIKS cell line is capable of producing cornified envelopes when induced to differentiate, the cells were removed from adherent culture and suspended for 24 hours in medium made semi-solid with methylcellulose. Many aspects of terminal differentiation, including differential expression of keratins and cornified envelope formation can be triggered in vitro by loss of keratinocyte cell-cell and cell-substratum adhesion. The NIKS keratinocytes produced as many as and usually more cornified envelopes than the parental keratinocytes. These findings demonstrate that the NIKS keratinocytes are not defective in their ability to initiate the formation of this cell type-specific differentiation structure.

To confirm that the NIKS keratinocytes can undergo squamous differentiation, the cells were cultivated in organotypic culture. Keratinocyte cultures grown on plastic substrata and submerged in medium replicate but exhibit limited differentiation. Specifically, human keratinocytes become confluent and undergo limited stratification producing a sheet consisting of 3 or more layers of keratinocytes. By light and electron microscopy there are striking differences between the architecture of the multilayered sheets formed in submerged culture and intact human skin. In contrast, organotypic culturing techniques allow for keratinocyte growth and differentiation under in vivo-like conditions. Specifically, the cells adhere to a physiological substratum consisting of dermal fibroblasts embedded within a fibrillar collagen base. The organotypic culture is maintained at the air-medium interface. In this way, cells in the upper sheets are air-exposed while the proliferating basal cells remain closest to the gradient of nutrients provided by diffusion through the collagen gel. Under these conditions, correct tissue architecture is formed. Several characteristics of a normal differentiating epidermis are evident. In both the parental cells and the NIKS cell line a single layer of cuboidal basal cells rests at the junction of the epidermis and the dermal equivalent. The rounded morphology and high nuclear to cytoplasmic ratio is indicative of an actively dividing population of keratinocytes. In normal human epidermis, as the basal cells divide they give rise to daughter cells that migrate upwards into the differentiating layers of the tissue. The daughter cells increase in size and become flattened and squamous. Eventually these cells enucleate and form cornified, keratinized structures. This normal differentiation process is evident in the upper layers of both the parental cells and the NIKS cells. The appearance of flattened squamous cells is evident in the upper epidermal layers and demonstrates that stratification has occurred in the organotypic cultures. In the uppermost part of the organotypic cultures the enucleated squames peel off the top of the culture. To date, no histological differences in differentiation at the light microscope level between the parental keratinocytes and the NIKS keratinocyte cell line grown in organotypic culture have been observed.

To observe more detailed characteristics of the parental (passage 5) and NIKS (passage 38) organotypic cultures and to confirm the histological observations, samples were analyzed using electron microscopy. Parental cells and the immortalized NIKS human keratinocyte cell line were harvested after 15 days in organotypic culture and sectioned perpendicular to the basal layer to show the extent of stratification. Both the parental cells and the NIKS cell line undergo extensive stratification in organotypic culture and form structures that are characteristic of normal human epidermis. Abundant desmosomes are formed in organotypic cultures of parental cells and the NIKS cell line. The formation of a basal lamina and associated hemidesmosomes in the basal keratinocyte layers of both the parental cells and the cell line was also noted.

Hemidesmosomes are specialized structures that increase adhesion of the keratinocytes to the basal lamina and help maintain the integrity and strength of the tissue. The presence of these structures was especially evident in areas where the parental cells or the NIKS cells had attached directly to the porous support. These findings are consistent with earlier ultrastructural findings using human foreskin keratinocytes cultured on a fibroblast-containing porous support. Analysis at both the light and electron microscopic levels demonstrate that the NIKS cell line in organotypic culture can stratify, differentiate, and form structures such as desmosomes, basal lamina, and hemidesmosomes found in normal human epidermis.

B) Cryopreservation

The present invention provides cryopreserved viable skin equivalents. The cryopreserved skin equivalents are preferable storable at approximately −50 C, −60 C, −70 C, −80 C or colder for an extended period of time such as greater than 1, 2, 3, 4, 5 or 6 months and up to 12 or 24 months without a substantial loss of viability.

In preferred embodiments, all steps of the cryopreservation process prior to product packaging are performed aseptically inside a Class 100 biosafety cabinet in a Class 10,000 cleanroom. In some embodiments, the cryopreservation process comprises treating an organotypically cultured skin equivalent in a cryoprotectant solution. Certain embodiments of the present invention are not limited to the use of any particular cryoprotectant. In some preferred embodiments, the cryoprotectant is glycerol. The cryoprotectant may be provided in different concentrations in the cryoprotectant solution. In some embodiments, the cryoprotectant is provided in a solution comprising about 20% or 21% to about 70% of the solution by volume, and more preferably about 20% or 21% to about 45% of the solution by volume or 37.5% to 62.5% of the solution by volume, or most preferably from about 25% to 40% of the solution by volume or 42.5% to 57.5% of the solution by volume, depending on the temperature. In some embodiments, the cryoprotectant solution preferably comprises about 32.5% v/v or about 50% v/v cryoprotectant (e.g., glycerol). In some embodiments, the cryoprotectant is provided in a base medium solution. Suitable base medium solutions include, but are not limited to, DMEM, Ham's F-10, Ham's F-12, DMEM/F-12, Medium 199, MEM and RPMI. In some embodiments, the base medium forms the remainder of the solution volume. In some embodiments, the cryoprotectant solution is buffered. Suitable buffers include, but are not limited to, HEPES, Tris, MOPS, and Trizma buffers. Buffering agents may be included at an amount to provide a buffered system in the range of pH 7.0 to 7.4. In some preferred embodiments, the cryoprotectant solution is buffered with from about 5 mM to 15 mM HEPES, most preferably about 10 mM HEPES to a pH of about 7.0 to 7.4.

In some particularly preferred embodiments, treatment with the cryoprotectant solution is conducted in a single step. By "single step" it is meant that the cryoprotectant solution is not exchanged during the equilibration procedure as is common in the art. For example, the treatment step is performed using a cryoprotectant solution with a defined concentration of cryoprotectant as opposed to a stepwise equilibration procedure where several media changes with increasing concentrations of cryoprotectant at each step. In some embodiments, the treatment step is conducted at a reduced temperature. In preferred embodiments, the treatment step is conducted at from about 2 C to 8 C, while in other embodiments, the treatment step is conducted at room temperature, for example from about 15 C to 30 C. In some embodiments, the skin equivalent is incubated in the cryoprotectant solution for about 10 to 60 minutes, preferably from about 20 to 30 minutes.

In some embodiments, the skin equivalent is frozen following treatment with the cryoprotectant solution. In some embodiments, excess cryoprotectant solution is removed from the skin equivalent prior to freezing, for example by aspirating the solution or moving the treated skin equivalent to a fresh vessel. Accordingly, in some embodiments, the treated skin equivalent is frozen by exposure to temperatures ranging from about −50 C to −100 C, and most preferably at about −80 C. In some preferred embodiments treated the skin equivalent is simply placed in a bag or other vessel such as a culture dish and placed in a freezing unit such as a low temperature (e.g., −80 C freezer) freezing unit. In contrast, it is common in the art to control the rate of freezing either by controlling the temperature in the freezing unit or by placing the tissue to be frozen in a container that allows control of the rate of decrease in temperature. In some embodiments, the treated skin equivalent is placed in a sterile culture vessel for freezing. The term "culture vessel" refers to any vessel of the type commonly used to culture cells or tissues and include circular, rectangular, and square dishes formed from a suitable material such as tissue culture plastic, polystyrene, polymers, plastics, glass, etc.

In some embodiments, the cryopreserved skin equivalent is packaged for long term storage. In some preferred embodiments, the skin equivalent is placed in a bag or culture vessel as described above. In some embodiments, the bag or culture vessel is sealed, preferably heat sealed in a sterile bag (e.g., a plastic or polymer bag) to provide a primary package. The primary package is then sealed inside a secondary bag, for example a secondary plastic, foil, or Mylar bag. The cryopreserved tissues of the present invention may preferably be stored at low temperature, from about −50 C to about −100 C, preferably about −80 C. The skin equivalents may be preferably stored from about 1, 2, 3, 4, 5 or 6 months and up to 12 or 24 months without a substantial loss of viability.

In some embodiments, the present invention provides a method of thawing a cryopreserved skin equivalent prior to application to a subject, comprising warming said cryopreserved skin equivalent and contacting said cryopreserved skin equivalent with an absorbent medium comprising a tissue compatible solution to allow removal of said cryoprotectant solution by diffusion. In some embodiments, the cryopreserved skin equivalent in a suitable bag or culture vessel is simply placed on a bench or table top and allowed to thaw. Thawing under controlled conditions as is common in the art is not necessary. In some embodiments, cryopreserved skin equivalent is placed on an absorbent medium to remove thawed cryoprotectant solution from the skin equivalent. The present invention is not limited to the use a particular absorbent medium. Suitable absorbent media include, but are not limited to, Telfa pads, cellulosic pads (e.g., Whatman 1003-090 filter pads and Pall 70010 filter pads), gauze pads, and foam pads (e.g., Covidien 55544 hydrophilic foam pad). In some preferred embodiments, the absorbent medium is a Telfa pad. In some embodiments, the absorbent medium comprises a tissue-compatible solution. In some embodiments, the tissue compatible solution is a buffered solution. Suitable tissue compatible solutions include, but are not limited to, DMEM, Ham's F-10, Ham's F-12, DMEM/F-12, Medium 199, MEM and RPMI. Suitable buffers include, but are not limited to, HEPES, Tris, MOPS, and Trizma buffers. Buffering agents may be included at an amount to provide a buffered system in the range of pH 7.0 to 7.4.

In further embodiments, the present invention provides kits comprising a cryopreserved skin substitute, preferably provided in a package as described above. In some embodiments, the kits further comprise an absorbent medium, and a tissue compatible solution.

In some embodiments, the present invention provides a process for forming an organotypically cultured skin equivalent and freezing the skin equivalent in the same culture vessel. In some embodiments, the culture vessel comprises an insert movable between upper and lower positions in the culture dish. The insert preferably comprises a bottom surface which is a porous membrane. In use, the vessel is filled with the appropriate culture medium and a dermal equivalent is formed on the porous membrane. The dermal equivalent is then seeded with keratinocytes (e.g., NIKS cells) in the presence of the appropriate culture medium. At the appropriate time, an air interface is created by lowering the level of culture medium in the vessel and the culture is continued until the stratified skin equivalent is formed. The culture medium is then removed from the vessel and the insert is lowered to the lower position. The cryoprotectant solution is added for treatment and then removed, and the vessel is then transferred to the freezing unit.

C) Therapeutic Uses

It is contemplated that the cryopreserved skin equivalents of the present invention may be used therapeutically. In some embodiments, the cryopreserved skin substitute is used in wound closure and burn treatment applications. The use of autografts and allografts for the treatment of burns and wound closure is described in Myers et al., A. J. Surg.

170(1):75-83 (1995) and U.S. Pat. Nos. 5,693,332; 5,658,331; and 6,039,760, each of which is incorporated herein by reference. In some embodiments, the skin equivalents may be used in conjunction with dermal replacements such as DERMAGRAFT or INTEGRA. Accordingly, the present invention provides methods for wound closure, including ulcers or wounds caused by burns, comprising providing a skin equivalent and a patient suffering from a wound and treating the patient with the skin equivalent under conditions such that the wound is closed.

In some embodiments, the skin equivalents are utilized to treat chronic skin wounds. Chronic skin wounds (e.g., venous ulcers, diabetic ulcers, pressure ulcers) are a serious problem. The healing of such a wound often takes well over a year of treatment. Treatment options currently include dressings and debridement (use of chemicals or surgery to clear away necrotic tissue), and/or antibiotics in the case of infection. These treatment options take extended periods of time and high levels of patient compliance. As such, a therapy that can increase a practitioner's success in healing chronic wounds and accelerate the rate of wound healing would meet an unmet need in the field. Accordingly, the present invention contemplates treatment of skin wounds with cryopreserved skin equivalents. In some embodiments, skin equivalents are topically applied to wounds. In other embodiments, cryopreserved skin equivalents are used for application to partial thickness wounds. In other embodiments, cryopreserved skin equivalents are used to treat full thickness wounds. In other embodiments, cryopreserved skin equivalents are used to treat numerous types of internal wounds, including, but not limited to, internal wounds of the mucous membranes that line the gastrointestinal tract, ulcerative colitis, and inflammation of mucous membranes that may be caused by cancer therapies. In still other embodiments, skin equivalents expressing host defense peptides or pro-angiogenic factors are used as a temporary or permanent wound dressing.

In still further embodiments, the cells are engineered to provide additional therapeutic agents to a subject. The present invention is not limited to the delivery of any particular therapeutic agent. Indeed, it is contemplated that a variety of therapeutic agents may be delivered to the subject, including, but not limited to, enzymes, peptides, peptide hormones, other proteins, ribosomal RNA, ribozymes, small interfering RNA (siRNA) micro RNA (miRNA), and antisense RNA. In preferred embodiments, the agents are host defense peptides such as human beta-defensin 1, 2, or 3 or cathelicidin or other proteins such as VEGF and HIF-1α, see, e.g., U.S. Pat. Nos. 7,674,291; 7,807,148; 7,915,042; 7,988,959; and 8,092,531; each of which is incorporated herein by reference in its entirety. These therapeutic agents may be delivered for a variety of purposes, including but not limited to the purpose of correcting genetic defects. In some particular preferred embodiments, the therapeutic agent is delivered for the purpose of detoxifying a patient with an inherited inborn error of metabolism (e.g., aminoacidopathesis) in which the skin equivalent serves as wild-type tissue. It is contemplated that delivery of the therapeutic agent corrects the defect. In some embodiments, the cells are transfected with a DNA construct encoding a therapeutic agent (e.g., insulin, clotting factor IX, erythropoietin, etc.) and skin equivalents prepared from transfected cells are administered to the subject. The therapeutic agent is then delivered to the patient's bloodstream or other tissues from the graft. In preferred embodiments, the nucleic acid encoding the therapeutic agent is operably linked to a suitable promoter. The present invention is not limited to the use of any particular promoter. Indeed, the use of a variety of promoters is contemplated, including, but not limited to, inducible, constitutive, tissue-specific, and keratinocyte-specific promoters. In some embodiments, the nucleic acid encoding the therapeutic agent is introduced directly into the keratinocytes (i.e., by electroporation, calcium phosphate co-precipitation, or liposome transfection). In other preferred embodiments, the nucleic acid encoding the therapeutic agent is provided as a vector and the vector is introduced into the keratinocytes by methods known in the art. In some embodiments, the vector is an episomal vector such as a replicating plasmid. In other embodiments, the vector integrates into the genome of the keratinocytes. Examples of integrating vectors include, but are not limited to, retroviral vectors, adeno-associated virus vectors, non-replicating plasmid vectors and transposon vectors.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: eq (equivalents); M (Molar); mM (millimolar); µM (micromolar); N (Normal); mol (moles); mmol (millimoles); µmol (micromoles); nmol (nanomoles); g (grams); mg (milligrams); µg (micrograms); ng (nanograms); l or L (liters); ml or mL (milliliters); µL or µL (microliters); cm (centimeters); mm (millimeters); µm (micrometers); nm (nanometers); C (degrees Centigrade); U (units), mU (milliunits); min. (minutes); sec. (seconds); % (percent); kb (kilobase); by (base pair); PCR (polymerase chain reaction); BSA (bovine serum albumin); CFU (colony forming units); kGy (kiloGray); PVDF (polyvinylidine fluoride); BCA (bicinchoninic acid); SDS-PAGE (sodium dodecyl sulfate polyacrylamide gel electrophoresis).

Example 1

StrataGraft® skin tissue is a living, full-thickness, allogeneic human skin substitute that reproduces many of the structural and biological properties of normal human skin. StrataGraft® skin tissue contains both a viable, fully-stratified epidermal layer derived from NIKS® cells, which are a consistent and well-characterized source of pathogen-free human keratinocyte progenitors, and a dermal layer containing normal human dermal fibroblasts (NHDF) embedded in a collagen-rich matrix. StrataGraft® skin tissue possesses excellent tensile strength and handling characteristics that enable it to be meshed, stapled, and sutured similarly to human skin grafts. StrataGraft® also exhibits barrier function comparable to that of intact human skin and is capable of delivering bioactive molecules for wound bed conditioning and tissue regeneration. The physical and biological characteristics of StrataGraft® skin tissue make it ideal for the treatment of a variety of skin wounds.

The manufacturing process for StrataGraft® skin tissue encompasses three sequential cell and tissue culture processes. In Stage I of the manufacturing process, NIKS keratinocytes are expanded in monolayer cell culture. Concurrent with the NIKS keratinocyte culture in Stage I, NHDF are expanded in monolayer culture and combined with purified type I collagen and culture medium and allowed to gel to form the cellularized dermal equivalent (DE). Alternatively, NHDF are seeded into Transwell inserts and allowed to proliferate and secrete and assemble extracellular matrix molecules into a simplified dermal equivalent. In Stage II, NIKS keratinocytes are seeded onto the surface of the DE and cultured under submerged conditions for two days to promote complete epithelialization of the DE surface. The tissue is then lifted to the air-liquid interface in Stage III, where it is maintained for 18 days in a controlled, low humidity environment to promote tissue maturation. The skin equivalents are generally prepared as described in U.S. Pat. Nos. 7,674,291; 7,807,148; 7,915,042; 7,988,959; and 8,092,531; each of which is incorporated herein by reference in its entirety.

Example 2

This example describes improved cryopreservation methods for human skin equivalents. The production process is unchanged from the current method described above. All tissues in the lot are fed with fresh medium and incubated overnight prior to cryopreservation. Prior to cryopreservation, media samples from all tissues in each lot are tested for sterility. The remaining tissues in each lot are cryopreserved as follows.

| Parameter | Operating Range |
|---|---|
| Cryoprotectant formulation | 50% (v/v) glycerol<br>DMEM (1X)<br>10 mM HEPES (pH 7.0 to 7.4) |
| Pre-freeze cryoprotectant incubation temperature | 2-8° C. |
| Pre-freeze cryoprotectant incubation time | 20-30 minutes |
| Freeze method | Direct transfer to −80° C. freezer |
| Storage temperature | −70 to −90° C. |
| Shipping conditions | Overnight delivery on dry ice |

Cryopreservation Process Description

All steps of the cryopreservation process prior to the final product packaging step are performed aseptically inside a Class 100 biosafety cabinet in a Class 10,000 cleanroom.

Step 1—Pre-cool 100 mm culture dishes containing 20 ml of cryoprotectant solution to 2-8° C. on a stainless steel cold treatment surface inside biosafety cabinet. Temperature of cold treatment surface is maintained at 2-8° C. for several hours by contact with frozen gel packs submerged in water.

Step 2—Transfer Transwells containing StrataGraft® tissues into individual dishes containing pre-cooled cryoprotectant solution. Incubate tissues 20-30 minutes in cryoprotectant on the cold treatment surface.

Step 3—Transfer treated StrataGraft® tissues to new sterile 100 mm culture dishes containing final product label so that the tissue rests on the bottom of the culture dish and return tissues back to the cold treatment surface. Excess cryoprotectant is allowed to drain from the skin equivalent to provide a treated skin equivalent that is substantially free of excess cryoprotectant on the exterior surfaces of the skin equivalent.

Step 4—Heat-seal 100 mm culture dishes in clear, sterile bags. Place primary package into secondary Mylar bag, heat-seal, and transfer packaged tissues to cold storage container until all tissues are packaged.

Step 5—Remove cold storage container with packaged StrataGraft® tissues from cleanroom and transfer tissues to an ultralow freezer (−75° C. to −80° C.). Place tissues in a pre-cooled rack in the freezer that allows unrestricted airflow to the top and bottom of the packaged tissues to ensure uniform and rapid cooling. Leave tissues undisturbed overnight during the freezing process.

Tissues are placed into quarantine storage at −70 to −90° C. pending results of lot release testing. A representative tissue from each lot of cryopreserved StrataGraft® skin tissue is tested using a panel of Quality Control SOP that have historically been used for lot release testing of StrataGraft® tissue.

Stratatech has established and qualified a panel of lot release assays that are used to characterize StrataGraft® skin tissue. A subset of these lot release assays has been used to monitor and evaluate the impact that changes to the storage conditions may have on key biological and structural characteristics of StrataGraft® skin tissue (e.g., barrier function, viability, and histological appearance). Although transient minor changes in the histological appearance of StrataGraft® tissue are generally observed following cryopreservation, the histological architecture normalizes after being reintroduced into organotypic culture for several days, indicating that the viable cells in the basal layer of StrataGraft® are able to proliferate and reproduce the epidermal layer after cryopreservation. The systematic evaluation of cryoprotectant concentration, incubation time, incubation temperature, freezing rate, and storage conditions has enabled Stratatech to identify a cryopreservation process that enables long-term storage of StrataGraft® skin tissue with consistent and defined quality and that meets the specifications that define StrataGraft® skin tissue.

The following parameters were systematically evaluated during development of the StrataGraft cryopreservation process.

Cryoprotectant composition
Pre-freeze cryoprotectant incubation temperature
Pre-freeze cryoprotectant incubation time
Number of steps required during cryoprotectant incubation
Freezing rate
Final product packaging
Storage temperature
Shipping conditions
Thaw temperature and time
Post-thaw cryoprotectant diffusion mediator
Post-thaw incubation solution
Post-thaw incubation temperature
Post-thaw incubation time As anticipated, many of these individual parameters interact to influence the properties of cryopreserved tissue. For example, it is not possible to optimize cryoprotectant concentration without also taking into account the cryoprotectant incubation time and temperature. Likewise, post-thaw incubation temperature influences the allowable range of post-thaw incubation times. During development of the cryopreservation process, a range of acceptable values for each of the individual parameters was identified and used to define the final combination of cryoprotectant formulation, pre-freeze incubation time, pre-freeze incubation temperature, freeze rate, and storage condition. The operating parameters of the cryopreservation process as developed for cryopreservation and storage of StrataGraft® skin tissue are listed above.

Glycerol (glycerin) was identified as the most desirable cryoprotectant for StrataGraft® tissue. The glycerol used in the cryoprotectant formulation is synthetic, USP-grade material that undergoes additional testing for endotoxin prior to release for use. In addition to glycerol, the cryoprotectant solution contains Dulbecco's Modified Eagle Medium (DMEM) and 10 mM HEPES to maintain pH of 7.0 to 7.4 at ambient atmospheric conditions. DMEM was chosen as the base for the cryopreservation solution because it is already a component of the culture medium used to prepare StrataGraft® skin tissue. HEPES is a well-characterized buffering agent that maintains the pH of the cryopreservation solution outside of a $CO_2$ environment.

A series of studies were performed to determine an appropriate glycerol concentration for use in the cryoprotectant solution. Glycerol concentrations tested ranged from 16.25% to 65%. In some cases, the concentration of glycerol was gradually increased in two or three steps by incubation in a series of solutions with increasing glycerol concentration. Initial studies to demonstrate the feasibility of cryopreserving StrataGraft® tissue used a three-step process in which the glycerol concentration was sequentially increased to 16.25%, then 32.5%, and finally to 65% by incubation for 15-20 minutes in each glycerol solution, while gradually reducing the temperature at each incubation step (16.25% glycerol incubation at room temperature, 32.5% at 2-8° C., and 65% at −20° C.). Finally, tissues were frozen to −140° C. at −15° C./min in a controlled-rate freezer. Cryopreserved tissues were transferred to an ultra-cold freezer (−80° C.), where they were maintained until thawed for analysis. While this three-step process could be used to preserve the viability and histological architecture of StrataGraft® tissues during cryopreserved storage, the complexity of having multiple steps with different solutions performed at different temperatures introduces the opportunity for error and is not amenable to process scale-up that would be required for commercialization.

Analysis of tissues cryopreserved with this three-step method revealed that, after thawing and dilution of the cryoprotectant, the tissues exhibited viability (assessed by the ability of viable cells in the tissue to convert MTT to its formazan product), histological architecture, and barrier function comparable to tissues that were not cryopreserved. The tissues maintained high levels of viability following re-introduction into organotypic culture for up to nine days after thawing, demonstrating that the metabolic activity detected shortly after thawing was not just residual enzymatic activity.

Figure 7:
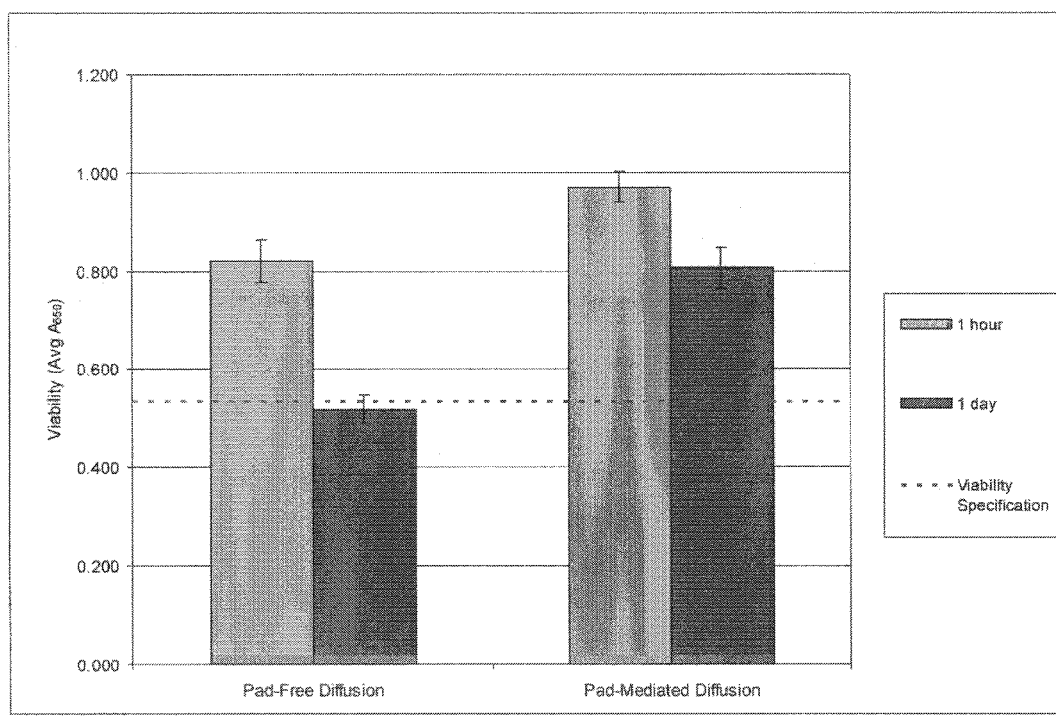
FIG. 7 is a graph of viability testing of thawed tissues using the MTT assay. The tissues were cryopreserved in 65% glycerol and then stored in vapor-phase LN$_2$ for 2 weeks. One tissue was thawed directly into a growth chamber without a cellulose pad, while the other was placed in a hold chamber, consisting of 2 cellulose filter pads on a raised stainless steel lifter, containing 100 ml of the growth media. The thawed tissues were held for 1 hour at 37° C. Tissues were analyzed after 1 hour and 1 day. Viability was measured by MTT analysis of three 0.5 cm$^2$ punches from each 44 cm$^2$ tissue at each time point (mean+/−1 st. dev.).

During these initial studies, it was found that the concentration of glycerol in cryopreserved tissues could be reduced after thawing either by incubating the tissues in a series of solutions with decreasing glycerol concentration, or by placing the tissues in a media reservoir with a filter pad just below the tissue to moderate the diffusion of glycerol. Based on these results, subsequent studies primarily used the single-step approach of incubating thawed tissues in culture medium with a pad to moderate glycerol diffusion. See FIG. 7.

Figure 5:
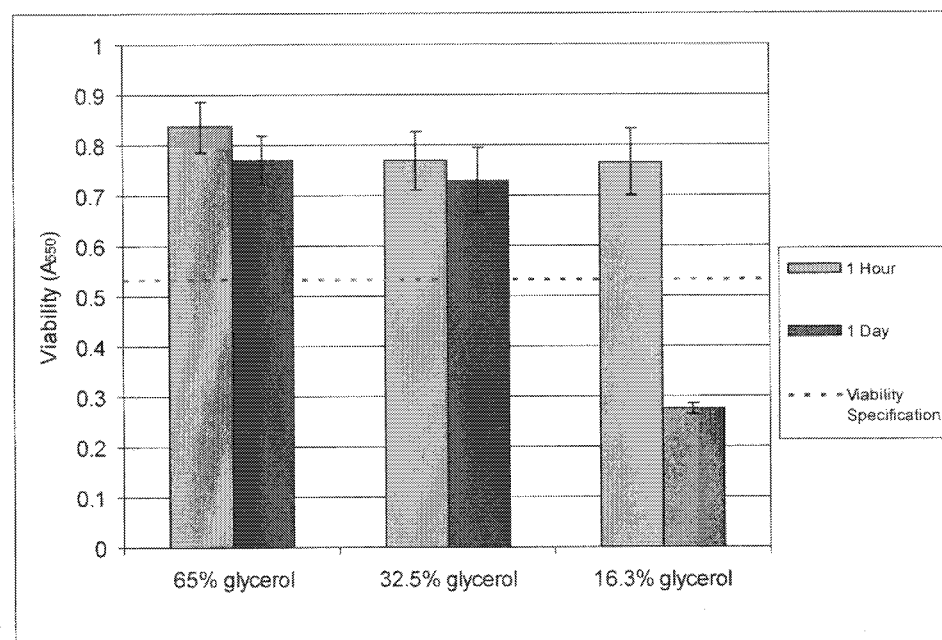
FIG. 5 is a graph of viability testing of thawed tissues using the MTT assay. The tissues were cryopreserved using a CRF following a stepwise temperature reduction (room temperature to 2-8° C. to −20° C.) during which the tissues were exposed to a graded series of glycerol concentrations soaked into sterile cellulose pads. All tissues were initially exposed to 16.3% glycerol at room temperature. Next, all tissues were switched to 2-8° C., with two tissues transferred to 32.5% glycerol. Lastly, all tissues were switched to −20° C., with one tissue transferred to 65% glycerol. Tissues were stored in vapor-phase LN2 for 6 days. Viability was measured by MTT analysis of three 0.5 cm$^2$ punches from each 44 cm$^2$ tissue at 1 hour and 1 day post-thaw (mean+/−1 st. dev.).

After demonstrating the feasibility of cryopreserving StrataGraft® skin tissue using the three-step method, we used this method as a benchmark against which to compare simplifications to the cryopreservation method. These studies examined reducing the number of steps required to reach the same final glycerol concentration (65%) or evaluating final glycerol concentrations that were lower than that used in the initial studies. Based on these studies, it was determined that glycerol concentrations as low as 32.5% could be used to reproducibly maintain the viability and histological architecture of StrataGraft® tissue during cryopreserved storage. In contrast, a final glycerol concentration of 16.25% in the cryoprotectant solution did not support maintenance of viability in frozen tissues. See FIG. 5. By evaluating a range of glycerol concentrations, it was determined that a cryoprotectant solution containing 50% glycerol reproducibly supported cryopreservation of StrataGraft® skin tissue and provided a margin of error above somewhat lower glycerol concentrations (e.g., 32.5%) that also supported efficient cryopreservation.

Pre-freeze Cryoprotectant Incubation Temperature, Incubation Time, and Number of Incubation Steps In addition to the concentration of glycerol in the cryoprotectant solution, three other factors affecting treatment of StrataGraft® tissue with cryoprotectant prior to cryopreservation are: 1) the pre-freeze cryoprotectant incubation time, 2) the temperature at which the tissues are treated with cryoprotectant, and 3) the number of steps required to reach the final glycerol concentration. As described above, initial feasibility studies with the three-step process involved sequentially incubating the tissues in solutions with increasing glycerol concentrations at successively lower temperatures for 15-20 minutes at each step. As stated above, a simpler cryopreservation process is preferred to avoid the complexity of having multiple steps with different solutions performed at different temperatures to reduce the opportunity for error and facilitate process scale-up. Toward this goal, the need for stepwise increase in cryoprotectant concentration and stepwise reduction in temperature during the pre-freeze cryoprotectant equilibration phase was evaluated.

In a series of studies performed in conjunction with evaluation of different cryoprotectant concentrations, it was determined that StrataGraft® tissues treated with cryoprotectant solutions containing 32.5, 50, or 65% glycerol in a single step at 2-8° C. for as little as 15 minutes and as long as 60 minutes were all able to withstand cryopreservation with minimal loss of viability or epidermal architecture. Although no decline in tissue performance was observed with cryoprotectant treatment times up to 60 minutes, relatively short glycerol treatment times (20 to 30 minutes) were chosen in order to minimize any potential adverse effects of prolonged exposure to cryoprotectant prior to freezing.

Freezing Rate

As described above, the initial feasibility studies utilized a controlled-rate freezer to freeze tissues at a rate of −15° C./min after equilibration with cryoprotectant. However, the use of a controlled-rate freezer would impose significant additional costs and is not amenable to process scale-up. Historically, cryopreservation of human cells has been accomplished at a more moderate rate of approximately −1° C./min without the use of controlled-rate freezers. This is routinely accomplished by placing vials of cells in an ultra-cold freezer in an insulated box or container designed to moderate the cooling rate to approximately −1° C./min.

Process development studies were designed to determine whether StrataGraft® tissues could be cryopreserved without using a controlled-rate freezer. These studies demonstrated that tissues frozen by direct transfer to an ultra-cold freezer (approximately −80 C) after treatment with cryoprotectant performed as well as tissues frozen in a controlled-rate freezer. See FIG. 1.

Figure 2:
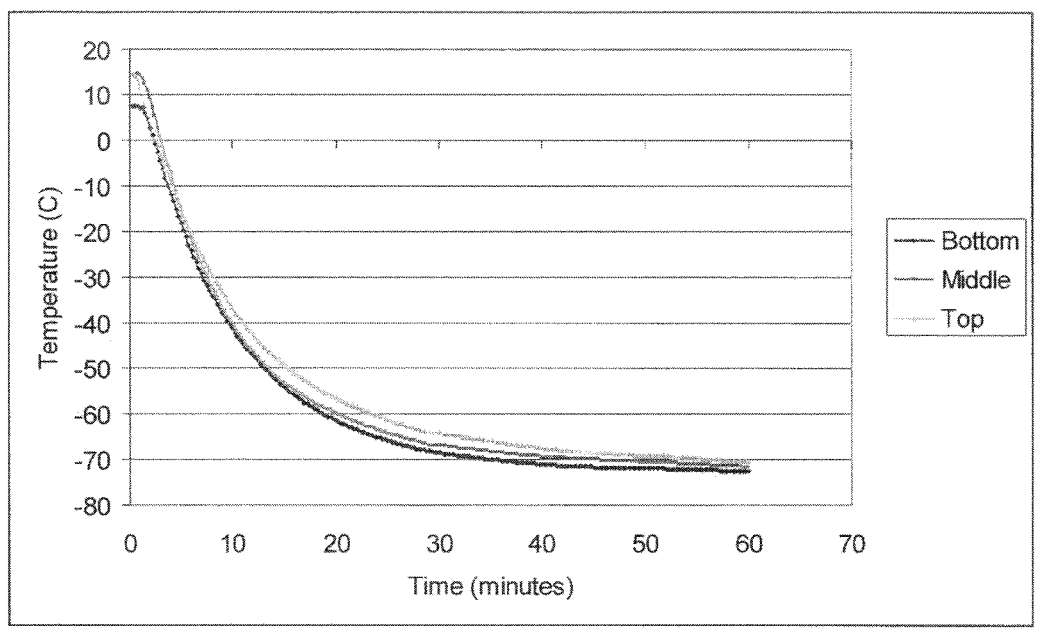
FIG. 2 is a temperature profile from a simulated passive tissue freeze. Temperature probes were affixed to the bottom of three 100 mm×20 mm dishes with a Transwell insert on top. The lid was placed on the dish and then they were packaged within an inner Whirl-pak pouch and an outer Mylar pouch and placed in an ultra-cold freezer set to −80° C. The packaged tissues were placed in a metal rack at a bottom, middle, and top position.

Temperature monitoring studies were performed to track the temperature of tissues during the cryopreservation process. Following packaging in an inner sterile bag and an outer Mylar bag, StrataGraft® tissues are transferred to a pre-cooled rack inside of an ultra-cold freezer. Each tissue is placed in a separate slot in the freezer rack, with ample room above and below the tissue to allow unrestricted airflow during the freezing process. Using temperature monitoring probes positioned within culture dishes packaged as described above and loaded into freezer racks in this configuration, the temperature rapidly decreases to approximately −50° C. within the first 15 minutes, further cools to approximately −65° C. by 30 minutes and reaches a final temperature of approximately −80° C. after three hours. There is no significant difference in the temperature profiles between tissues placed in the top, middle, and bottom positions of the freezer rack. See FIG. 2.

Final Product Packaging

In initial studies, tissues were frozen in contact with a layer of cryoprotectant solution after incubation with cryoprotectant. Although tissues cryopreserved in this manner exhibited good post-thaw properties, rapid thawing of tissues frozen in contact with this layer of cryoprotectant required incubation for several minutes in a 35-39° C. water bath, which would to be difficult to implement and standardize in a surgical suite. It was subsequently determined that contact with the cryoprotectant solution was not required after tissues had been treated with cryoprotectant. This enabled development of the final product configuration in which tissues are transferred to an empty sterile 100 mm culture dish after treatment with cryoprotectant, where they are frozen in contact with the bottom of the empty dish rather than being frozen in contact with a layer of cryoprotectant solution.

To maintain the sterility of cryopreserved tissues, the 100 mm culture dishes containing cryoprotectant-treated tissues are aseptically packaged and heat-sealed inside of a sterile polyethylene sample bag. The inner bag is then heat-sealed inside a puncture-resistant, food grade, metalized polyester/polyethylene bag, which protects the packaged tissues from light, moisture, and provides a barrier to $CO_2$ vapor during shipment on dry ice. The stability and comparability studies described below utilized tissues packaged and cryopreserved in this configuration.

Storage Temperature

Figure 3:
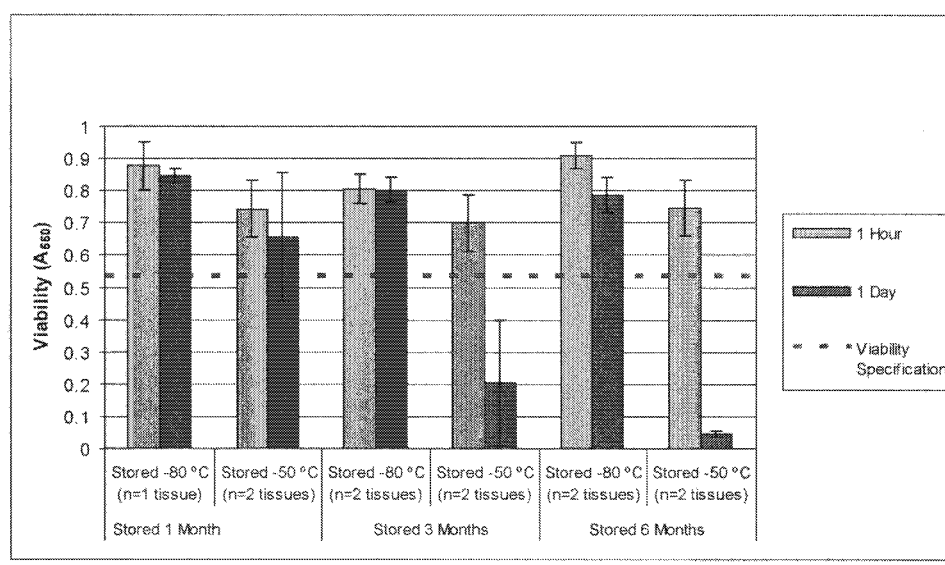
FIG. 3 is a graph of viability testing of thawed tissues using the MTT assay. The tissues were cryopreserved using a CRF and then stored in ultra-cold freezers set to −80° C. or −50° C. for 1 to 6 months, then thawed and analyzed at 1 hour and 1 day. Viability was measured by MTT analysis of three 0.5 cm$^2$ punches from each 44 cm$^2$ tissue at each time point (mean+/−1 st. dev.).

Cryopreservation of viable skin equivalents enables burn centers to have ready access to this cell-based regenerative medicine therapeutic for burns and other indications that require rapid intervention. Optimally, major burn centers would be able to maintain an inventory of the product for use without the need to schedule a delivery on a case by case basis. In early feasibility studies, cryopreserved tissues were stored at −196° C. in a vapor-phase nitrogen freezer. Since burn centers do not typically have liquid nitrogen storage capabilities, cryopreservation procedures were developed that permit storage of tissue for at least six months in ultra-cold freezers (−60° C. to −90° C.), which are readily available in blood and tissue banks at most hospitals and trauma centers. Results of these experiments, demonstrated that while tissues stored at −50° C. exhibited significant losses of viability over the course of several weeks, tissues stored at −80° C. retained levels of viability comparable to tissues that had been stored in nitrogen vapor. See FIG. 3. These results were obtained with several independent lots of cryopreserved tissue, confirming the reproducibility of this finding. As described in the Stability of Cryopreserved Tissues section below, analysis of tissues stored at −80° C. for six months revealed no significant loss of viability or changes to epidermal architecture during storage.

Shipping Conditions

Figure 4:
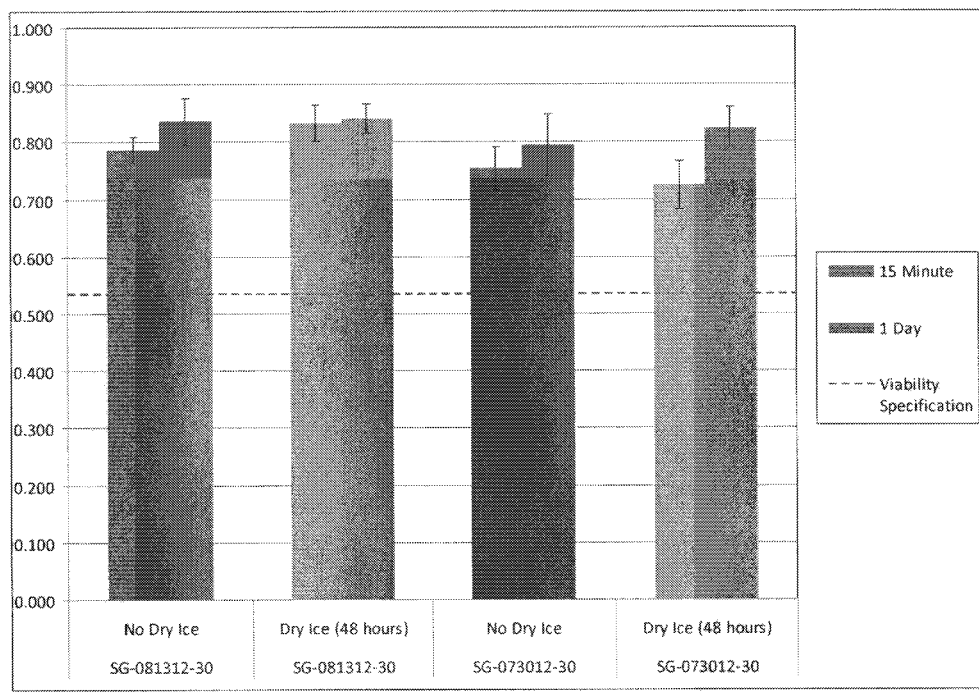
FIG. 4 is a graph of viability testing of thawed tissues using the MTT assay. Tissues from two independent lots were cryopreserved and then stored in an ultra-cold freezer set to −80° C. for greater than 1 month. Two tissues from each lot were placed into a container of dry ice for 48 hours, with two control tissues from each lot remaining in the ultra-cold freezer. At the end of the dry ice exposure, all tissues were thawed and analyzed at 15 minutes and 1 day. Viability was measured by MTT analysis of four 0.5 cm$^2$ punches from each 44 cm$^2$ tissue at each time point (mean+/−1 st. dev.).

Cryopreserved StrataGraft® skin tissue will be shipped to clinical sites on dry ice for next morning delivery via commercial courier such as FedEx or UPS. The shipping container (Freezetherm FT29, Laminar Medica) is a validated dry ice shipping box that holds sufficient dry ice to maintain the cryopreserved tissues at <−75° C. for at least 72 hours at ambient temperatures of up to 35° C. to account for possible delays in delivery. Experimental data indicates that storage of cryopreserved tissues in the dry ice shipping container for >48 hours does not have any detectable adverse effect on tissue viability or histological architecture. See FIG. 4. Following receipt at the clinical site, cryopreserved StrataGraft tissues will be stored in an ultra-cold freezer (e.g., −60° C. to −90° C.) until use.

Pre-operative Preparation of Cryopreserved Tissue

Prior to clinical use, cryopreserved StrataGraft tissue is thawed and incubated briefly on pads saturated with culture medium to remove residual cryoprotectant. Due to the geometry of the tissue, the thaw phase is rapid. After tissues are thawed, Transwell inserts containing the tissue are aseptically transferred to the sterile field and placed in sterile dishes containing absorbent pads saturated with culture medium. As described below, the timing of the post-thaw incubation phase is flexible enough to accommodate delays that could be reasonably anticipated during clinical use.

Thaw Temperature and Time

As described in the Final product packaging section above, tissues are cryopreserved in a culture dish without a layer of cryoprotectant solution, which allows the tissues to be thawed rapidly at ambient temperature simply by placing the package onto a bench or table. Precise control over the thaw temperature and time is not required, as experimental data shows that tissues thawed for varying times at temperatures ranging from 22° C. to 40° C. exhibit similar post-thaw properties.

Post-thaw Incubation Solution

Figure 6:
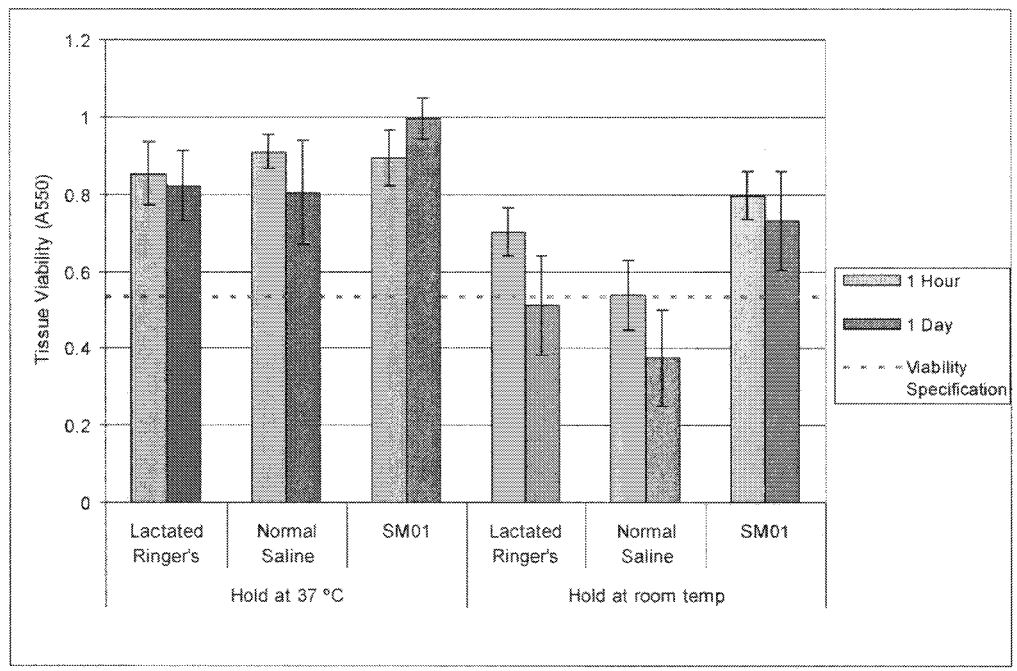
FIG. 6 is a graph of viability testing of thawed tissues using the MTT assay. The tissues were cryopreserved in 65% glycerol by passive freezing in an ultra-cold freezer set to −80° C. and then stored at −80° C. for 6 weeks. Tissues were thawed and placed in a hold chamber, consisting of two cellulose filter pads on a raised stainless steel lifter, containing 100 ml of the specified solution and held for 1 hour at the specified temperature. Tissues were analyzed after 1 hour and 1 day. Viability was measured by MTT analysis of three 0.5 cm$^2$ punches from each 44 cm$^2$ tissue at each time point (mean+/−1 st. dev.).

Buffered post-thaw incubation solutions work better than unbuffered solutions. Tissues incubated in simple unbuffered salt solutions (lactated Ringer's or normal saline) do not survive as well as tissues incubated in culture media-based solutions. Stratatech's SM01 culture media (StrataLife series) or commercially available DMEM/F12 media buffered with HEPES are preferred. See FIG. 6.

Post-thaw Incubation Temperature

Initial development studies found that buffered culture media were able to support tissue viability following post-thaw incubation at both 37 C and room temperature. However, warm post-thaw incubation temperatures (37 C) work better than cooler temps (20-25 C) for sub-optimal incubation solutions. See FIG. 6. Starting the post-thaw incubation on a pad containing 37 C media that slowly cools to room temp over the course of 15-30 minutes also works well. Higher temp seems to be most important in the first few minutes after thaw.

Figure 8:
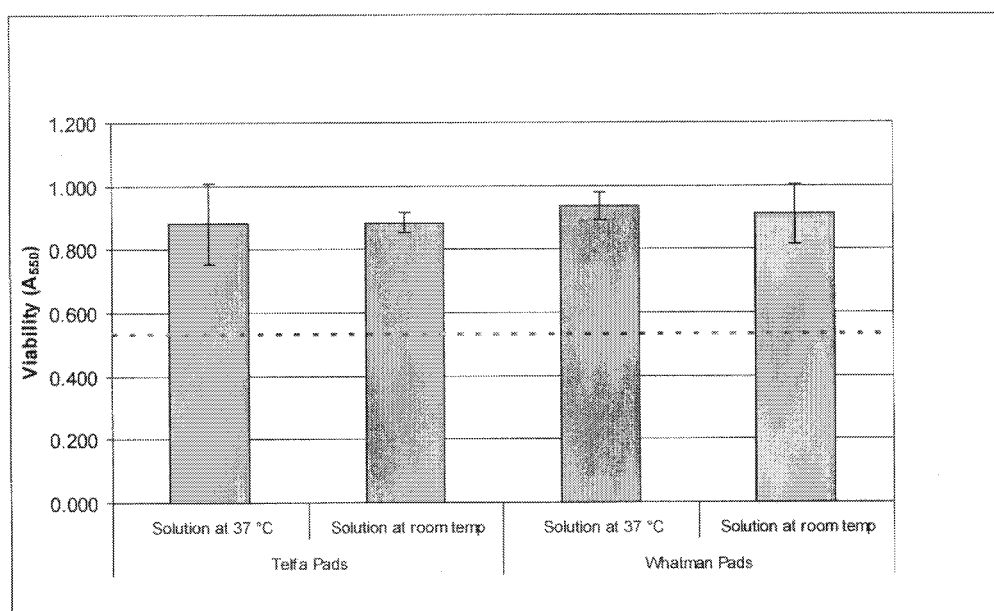
FIG. 8 is a graph of viability testing of thawed tissues using the MTT assay. Tissues from one lot were cryopreserved and then stored in an ultra-cold freezer set to −80° C. for 1 week. The tissues were thawed for 10 minutes, placed in hold chambers containing either Telfa pads or Whatman pads soaked with 40 ml of a buffered nutrient solution warmed to either 37° C. or room temperature (n=2 tissues per thaw condition). The tissues were placed in the hold chambers for 15-20 minutes, and then re-cultured in a growth chamber for 1 day. The tissues were analyzed at 1 day post-thaw. Viability was measured by MTT analysis of four 0.5 cm$^2$ punches from each 44 cm$^2$ tissue (mean+/−1 st. dev.). The viability specification is indicated by the red dashed line.

Later development studies demonstrated that buffered media solutions pre-warmed to only room temperature were comparable to media warmed to 37 C in their ability to support the properties of thawed tissues. This was true for tissues held on either Telfa pads or Whatman pads. See FIG. 8

Post-thaw Incubation Time

Tissues can be left on the media saturated pad for times ranging from 15 min to 4 hr at 20-25 C or up to 2 hr at 40 C with no significant effect on tissue viability.

Stability Study

Stability of Cryopreserved Tissues

Figure 9:
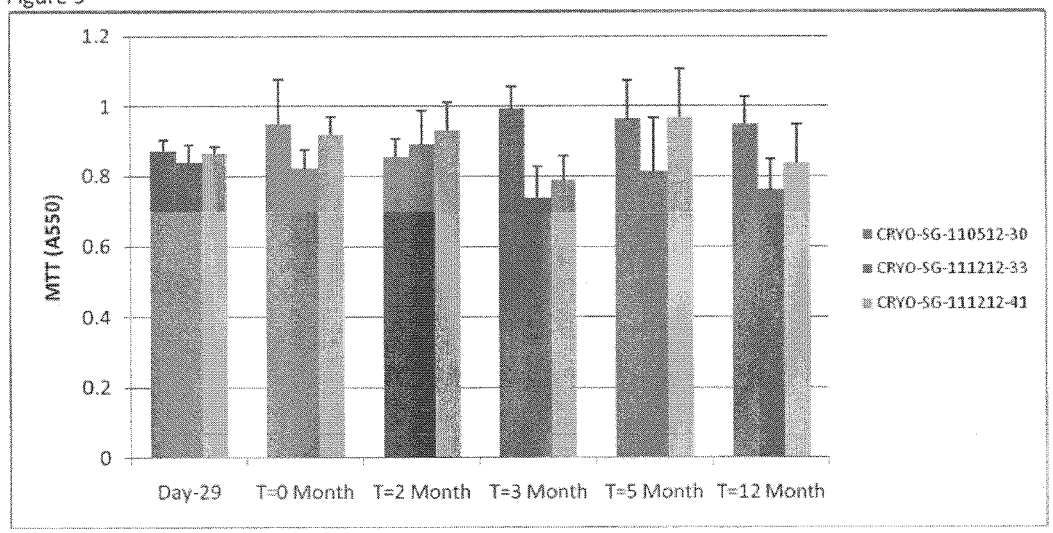
FIG. 9 is a graph of viability testing of thawed tissues using the MTT assay. Tissues from three independent lots were treated with 50% glycerol at 2 to 8° C. and cryopreserved as described in Example 2. Cryopreserved tissues were stored in an ultra-cold freezer at approximately −80° C. for up to 12 months. After 0, 2, 3, 5, and 12 months of storage, two tissues from each lot were thawed at room temperature and held on media saturated Telfa pads for 15 minutes. Tissues were then returned to culture overnight in a culture dish with a raised stainless steel lifter, containing 90 ml of growth media. Viability was measured by MTT analysis of four 0.5 cm$^2$ punches from each 44 cm$^2$ tissue at each time point (mean+/−1 st. dev.).

Although many of the studies described above analyzed tissues that had been stored in a frozen state for only a few days or weeks, it is widely accepted that the majority of damage to cryopreserved cells and tissues occurs during the freezing and thawing stages, with relatively little loss of cellular viability taking place during long-term storage at reduced temperatures. Long-term storage results show that cryopreserved StrataGraft® skin tissue maintains high levels of viability and histological architecture after at least 12 months of storage at ultracold temperatures. Analysis of tissues produced and cryopreserved using the cryopreservation process described above indicates that tissues cryopreserved with this process maintain key biological, structural, and physical properties during storage for at least 12 months at ultracold temperatures. See FIG. 9.

Example 3

This example describes improved cryopreservation methods for human skin equivalents utilizing a pre-freeze treatment step with cryopreservation solutions containing 32.5% or 50% glycerol at room temperature. The production process is unchanged from the current method described previously. At the end of the production process, the tissues are treated and cryopreserved as follows.

| Parameter | Operating Range |
|---|---|
| Cryoprotectant formulation | 32.5% (v/v) glycerol<br>DMEM (1X)<br>10 mM HEPES (pH 7.0 to 7.4)<br>or<br>50% (v/v) glycerol<br>DMEM (1X)<br>10 mM HEPES (pH 7.0 to 7.4) |
| Pre-freeze cryoprotectant incubation temperature | Room temperature |
| Pre-freeze cryoprotectant incubation time | 15-45 minutes |
| Freeze method | Direct transfer to −80° C. freezer |
| Storage temperature | −70 to −90° C. |
| Shipping conditions | Overnight delivery on dry ice |

Cryopreservation Process Description

All steps of the cryopreservation process prior to the final product packaging step are performed aseptically inside a Class 100 biosafety cabinet in a Class 10,000 cleanroom.

Step 1—Dispense 20 ml of cryoprotectant solution to 100 mm culture dishes.

Step 2—Transfer Transwells containing StrataGraft® tissues into individual dishes containing cryoprotectant solution. Incubate tissues 15-45 minutes in cryoprotectant.

Step 3—Transfer treated StrataGraft® tissues to new sterile 100 mm culture dishes containing final product label so that the tissue rests on the bottom of the culture dish. Excess cryoprotectant is allowed to drain from the skin equivalent to provide a treated skin equivalent that is substantially free of excess cryoprotectant on the exterior surfaces of the skin equivalent.

Step 4—Heat-seal 100 mm culture dishes in clear, sterile bags. Place primary package into secondary Mylar bag and heat-seal.

Step 5—Remove the packaged StrataGraft® tissues from cleanroom and transfer tissues to an ultralow freezer (−75° C. to −80° C.). Place tissues in a pre-cooled rack in the freezer that allows unrestricted airflow to the top and bottom of the packaged tissues to ensure uniform and rapid cooling. Leave tissues undisturbed overnight during the freezing process.

Figure 10:
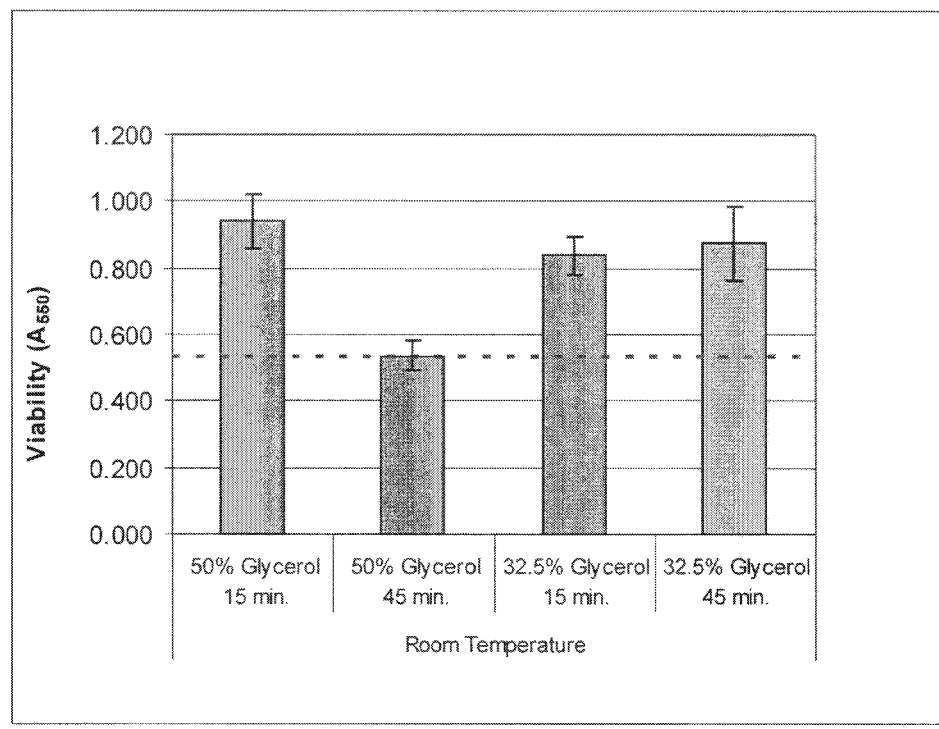
FIG. 10 is a graph of viability testing of thawed tissues using the MTT assay. Tissues from one lot were treated with the specified glycerol concentration (32.5% or 50%) at the listed conditions prior to the freeze and then stored in an ultra-cold freezer set to −80° C. for 9 days. The tissues were thawed for 10 minutes, placed on a Telfa stack soaked with 40 ml of a buffered nutrient solution for 15-20 minutes, and then re-cultured in a growth chamber for 1 day. The tissues were analyzed at 1 day post-thaw. Viability was measured by MTT analysis of four 0.5 cm$^2$ punches from each 44 cm$^2$ tissue (mean+/−1 st. dev.). The viability specification is indicated by the red dashed line.

Cryopreserved tissues were thawed at room temperature for 10 minutes, transferred to a hold chamber containing Telfa pads saturated with 40 ml of HEPES-buffered culture medium that had been warmed to room temperature, and held at RT for 15 to 20 minutes. Tissues were transferred to a culture dish containing 90 ml of SM01 medium and returned to culture overnight. Tissues were analyzed for viability after overnight re-culture. Tissues pre-treated with 32.5% glycerol at room temperature for 15 to 45 minutes had acceptable post-thaw viability. Tissues treated with 50% glycerol at room temperature for 15 minutes also had acceptable viability; however, tissues treated with 50% glycerol at room temperature for 45 minutes had unacceptable viability. See FIG. 10.

Example 4

MTT assays are preferably conducted as follows. Samples are excised from the skin tissue using an 8 mm biopsy punch. The samples are transferred to 0.3 ml MTT Assay Medium (1 mg/ml MTT reagent in Ham's F-12) in a 24-well plate that has been pre-warmed to 37° C./5% $CO_2$. The samples are incubated for 85-95 minutes at 37° C./5% $CO_2$. The samples are blotted and transferred to 2 ml isopropanol. The samples are thoroughly mixed to completely extract the purple formazan product. 200 μl in triplicate of each extract is aliquoted into a 96-well plate, using isopropanol as a blank. The absorbance (550 nm) is measured in a spectrophotometer.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in tissue culture, molecular biology, biochemistry, or related fields are intended to be within the scope of the following claims.

We claim:

1. A method of cryopreserving an organotypically cultured skin equivalent to maintain viable tissue comprising:
    treating an organotypically cultured skin equivalent in a cryoprotectant solution in a single step, wherein said organotypically cultured skin equivalent comprises stratified squamous epithelia on a dermal layer comprising fibroblasts embedded in collagen, and wherein the cryoprotectant solution comprises glycerol in an amount that is about 21% to about 70% of the cryoprotectant solution by volume;
    separating the treated organotypically cultured skin equivalent from excess cryoprotectant solution to provide a treated skin equivalent that is substantially free of excess cryoprotectant on the exterior surfaces of the skin equivalent;
    packaging said organotypically cultured skin equivalent in the absence of additional cryoprotectant to provide a packaged skin equivalent; and
    freezing said packaged organotypically cultured skin equivalent to provide a cryopreserved skin equivalent that retains viability after thawing.

2. The method of claim 1, wherein said freezing further comprises freezing at about −80 C.

3. The method of claim 1, wherein said freezing further comprises direct exposure to temperatures ranging from about −50 C. to −100 C.

4. The method of claim 1, wherein said packaging further comprises enclosing said cryopreserved skin equivalent in a sterile bag and enclosing said sterile bag in a second bag.

5. The method of claim 1, wherein said organotypically cultured skin equivalents comprise NIKS cells.

6. The method of claim 5, wherein said NIKS cells comprise an exogenous nucleic acid sequence encoding an exogenous polypeptide.

7. The method of claim 1, wherein said cryopreserved skin equivalent has an $A_{550}$ of at least 50% of a reference skin equivalent as determined by an MTT assay.

8. The method of claim 1, further comprising thawing said cryopreserved skin equivalent and applying said thawed skin equivalent to a patient in need thereof, wherein said thawed skin equivalent is not rinsed prior to said application to said patient.

9. A method of producing a cryopreserved skin equivalent comprising:
   providing a culture dish comprising an insert movable between upper and lower positions in said culture dish, said insert having a bottom planar surface formed from a porous membrane,
   forming a dermal equivalent comprising fibroblast cells on said porous membrane in said insert, wherein said insert is placed in said upper position in said culture dish,
   culturing said fibroblast cells to form a dermal equivalent,
   applying keratinocytes to said dermal equivalent,
   culturing said keratinocytes in a culture medium under conditions such that said keratinocytes form a skin equivalent comprising stratified epithelium,
   removing said culture medium,
   lowering said insert to said lower position,
   treating said skin equivalent with a cryoprotectant solution wherein the cryoprotectant solution comprises glycerol in an amount that is about 21% to about 70% of the cryoprotectant solution by volume,
   separating the treated organotypically cultured skin equivalent from excess cryoprotectant solution to provide a treated skin equivalent that is substantially free of excess cryoprotectant on the exterior surfaces of the skin equivalent, and
   freezing said skin equivalent in said culture dish in the absence of additional cryoprotectant to provide a cryopreserved skin equivalent that retains viability after thawing.

* * * * *